(12) United States Patent
Yousef et al.

(10) Patent No.: US 12,285,412 B1
(45) Date of Patent: Apr. 29, 2025

(54) ORGANOSELENIUM BENZIMIDAZOLE COMPOUNDS FOR TREATING CANCER

(71) Applicant: IMAM MOHAMMAD IBN SAUD ISLAMIC UNIVERSITY, Riyadh (SA)

(72) Inventors: Tarek Ahmed Yousef, Riyadh (SA); Saad Shaaban, Almansourah (EG); Ahmed A. Al-Karmalawy, Baghdad (IQ)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/003,381

(22) Filed: Dec. 27, 2024

(51) Int. Cl.
*A61K 31/4184* (2006.01)
*C07D 235/18* (2006.01)

(52) U.S. Cl.
CPC ........ *A61K 31/4184* (2013.01); *C07D 235/18* (2013.01)

(58) Field of Classification Search
CPC .......................... A61K 31/4184; C07D 235/18
See application file for complete search history.

(56) References Cited

U.S. PATENT DOCUMENTS

| | | |
|---|---|---|
| 2016/0082033 A1 | 3/2016 | Power et al. |
| 2022/0154003 A1 | 5/2022 | Vendrell et al. |

FOREIGN PATENT DOCUMENTS

| | | |
|---|---|---|
| CN | 105646476 B | 9/2018 |
| CN | 108675961 B | 4/2022 |

OTHER PUBLICATIONS

Joao M. Anghinoni et al., "Recent Advances in the Synthesis and Antioxidant Activity of Low Molecular Mass Orgampselenium Molecules", Molecules, vol. 28, Issue 21, Oct. 30, 2023, 45 Pages.
Yuanwei Liang, et al., "Microwave-Assisted Syntheses of Benzimidazole-Containing Selenadiazole Derivatives That Induce Cell-Cycle Arrest and Apoptosis in Human Breast Cancer Cells by Activation of the ROS/AKT Pathway", Chem Med Chem, vol. 11, Issue 20, Oct. 19, 2016. 2339-2346, 8 Pages.

*Primary Examiner* — Kamal A Saeed
(74) *Attorney, Agent, or Firm* — Oblon, McClelland, Maier & Neustadt, L.L.P.

(57) ABSTRACT

A method of treating cancer that includes administering a therapeutically effective amount of an organoselenium benzimidazole compound of Formula (I),

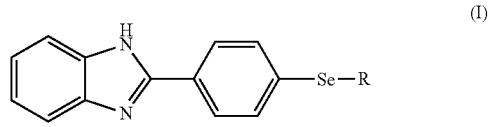

where R is at least one selected from the group consisting of an alkyl group having 1 to 6 carbon atoms, an unsubstituted benzyl group, a para halo-substituted benzyl group, and an allyl group.

19 Claims, 7 Drawing Sheets

ORGANOSELENIUM BENZIMIDAZOLE COMPOUNDS FOR TREATING CANCER

BACKGROUND

Technical Field

The present disclosure is directed to a method of treating cancer using organoselinium benzimidazole compounds.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Cancer is a leading cause of death worldwide, and its global rise is alarming, driven by genetic mutations that result in uncontrolled cell growth. In 2018, the World Health Organization's Annual Global Cancer Statistics indicated 18.1 million new cases and 9.6 million deaths. This rise is reflected in higher rates of both cancer diagnoses and deaths, emphasizing the urgent need for effective solutions. Early detection is crucial, and treatment options include surgery, chemotherapy, radiation, and targeted therapies such as immunotherapy.

To date, significant advances have been made in cancer prevention and therapy; however, toxic side effects, drug resistance, and treatment costs continue to pose substantial challenges. Natural and synthetic selenium compounds, along with nano-selenium particles, have gained attention as potential cancer-fighting agents. Organoselenium compounds are usually favored over inorganic selenium compounds due to their increased bioavailability and decreased toxicity.

Organoselenium compounds have received considerable attention as potential pharmaceutical compounds, play important roles in pharmaceutical formulations, are building blocks for complex molecules, and contribute to bioscience. These compounds exhibit two characteristics: acting as antioxidants in healthy cells and pro-oxidants in cancer cells. Various organoselenium compounds have been extensively studied due to their usefulness in biosynthesis. Interest in the biology of selenium was heightened when selenocysteine (Sec) was discovered as the 21st amino acid in the Se(II)/Se(IV) redox site of glutathione peroxidase (GPx), an enzyme essential for the redox cycle in living organisms. GPX enzymes exert antioxidant functions, utilizing glutathione to reduce harmful peroxides and protect lipid membranes from oxidative damage. Oxidative stress, characterized by the overproduction of reactive oxygen species (ROS) as a by-product of aerobic metabolism, is involved in various diseases. Organoselenium compounds can protect healthy cells from DNA damage by ROS, and their identified vaccines are correlated. Natural antioxidant enzymes such as catalase, superoxide dismutase, and GPX contribute to the reduction of excessive ROS levels in the biological system. Consequently, various organoselenium compounds have been developed to mimic the activity of GPX enzymes.

There still exists a need to develop organoselenium compounds with increased bioavailability and reduced toxicity for cancer treatment.

SUMMARY

According to a first aspect, the present disclosure relates to a method of treating cancer in a subject in need thereof. In some embodiments, the method involves administering a therapeutically effective amount of an organoselenium benzimidazole compound of Formula (I),

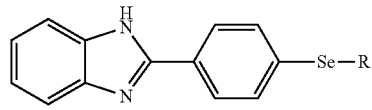

wherein, R is at least one selected from the group consisting of an alkyl group having 1 to 6 carbon atoms, an unsubstituted benzyl group, a para halo-substituted benzyl group, and an allyl group In some embodiments, the alkyl group having 1 to 6 carbon atoms is at least one selected from the group consisting of methyl, ethyl, and n-propyl.

In some embodiments, the organoselenium benzimidazole compound of Formula (I) is at least one selected from formulae (II) to (VII)

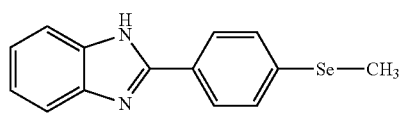

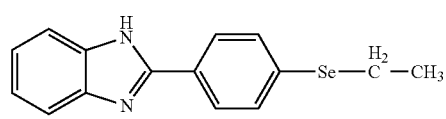

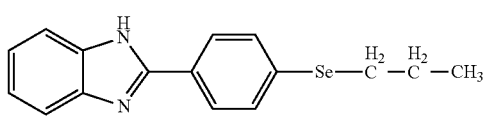

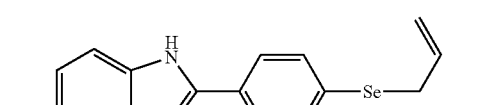

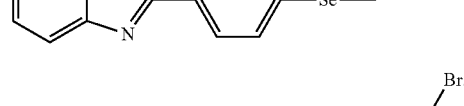

In some embodiments, the cancer is at least one selected from the group consisting of glioblastoma, colorectal cancer, lung cancer, head and neck cancer, gastric cancer, pancreatic cancer, breast cancer, ovarian cancer, hepatocellular carcinoma, renal cell cancer, liver cancer, B-cell lymphoma, and cervical cancer.

In some embodiments, the organoselenium benzimidazole compound of Formula (I) has a mechanism of action that includes inhibition of GPX4.

In some embodiments, the organoselenium benzimidazole compound of Formula (I) acts to inhibit GPX4 by binding to GPX4 with a binding affinity of −5.50 to −4.25 kcal/mol.

In some embodiments, the inhibition of GPX4 causes ferroptosis.

The present disclosure also relates to a pharmaceutical composition. In some embodiments, the pharmaceutical composition includes an organoselenium benzimidazole compound of Formula (I) or a pharmaceutically acceptable salt thereof; and a pharmaceutically acceptable carrier and/or excipient,

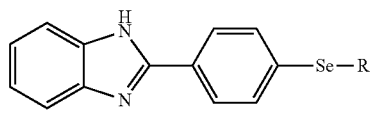

(I)

wherein, R is at least one selected from the group consisting of an alkyl group having 1 to 6 carbon atoms, an unsubstituted benzyl group, a para halo-substituted benzyl group, and an allyl group.

In some embodiments, the alkyl group having 1 to 6 carbon atoms is at least one selected from the group consisting of methyl, ethyl, and n-propyl.

In some embodiments, the organoselenium benzimidazole compound of Formula (I) is at least one selected from Formulae (II) to (VII)

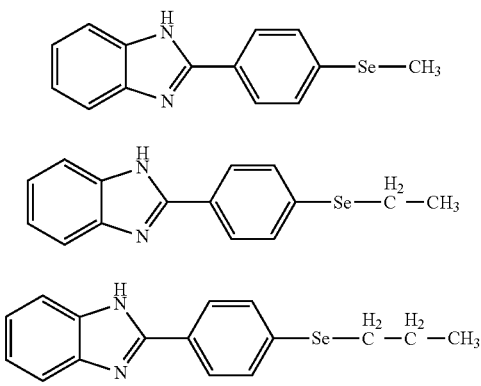

(II)

(III)

(IV)

(V)

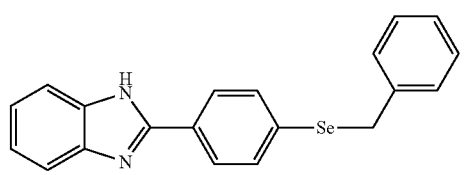

(VI)

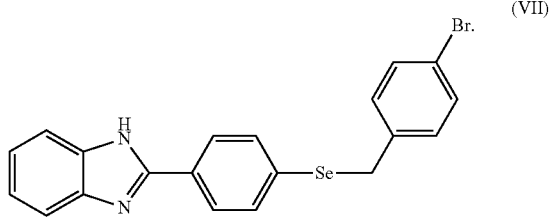

(VII)

In some embodiments, the pharmaceutically acceptable carrier and/or excipient is at least one selected from the group consisting of a buffer, an inorganic salt, a synthetic fatty acid, a vegetable oil, a fatty ester, a surfactant, and a polymer.

In some embodiments, the pharmaceutical composition further comprises one or more of a sweetener, a flavoring, and a colorant.

In some embodiments, the pharmaceutical composition is formulated for at least one mode of administration selected from the group consisting of oral administration, parenteral administration, rectal administration, topical administration, transdermal administration, intralesional administration, and inhalation administration.

In some embodiments, a method of forming an organoselenium benzimidazole compound of Formula I is described. The method includes reacting o-phenylenediamine and 4,4'-diselanediyldibenzoic acid with an acid to form 1,2-bis(4-(1H-benzo[d]imidazol-2-yl)phenyl)diselane; and reacting the 1,2-bis(4-(1H-benzo[d]imidazol-2-yl)phenyl)diselane with at least one selected from the group consisting of an alkyl halide having 1 to 6 carbon atoms, an unsubstituted benzyl halide, a para halo-substituted benzyl halide, and an allyl halide, a hydride reducing agent, and a base to form the organoselenium benzimidazole compound of Formula (1).

In some embodiments, the acid comprises acetic acid, polyphosphoric acid, and water.

In some embodiments, the method includes reacting o-phenylenediamine and 4,4'-diselanediyldibenzoic acid with an acid at 160 to 200° C.

In some embodiments, the alkyl group having 1 to 6 carbon atoms is at least one selected from the group consisting of methyl, ethyl, and n-propyl.

In some embodiments, the hydride reducing agent is sodium borohydride.

In some embodiments, the base is an alkali metal hydroxide base.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
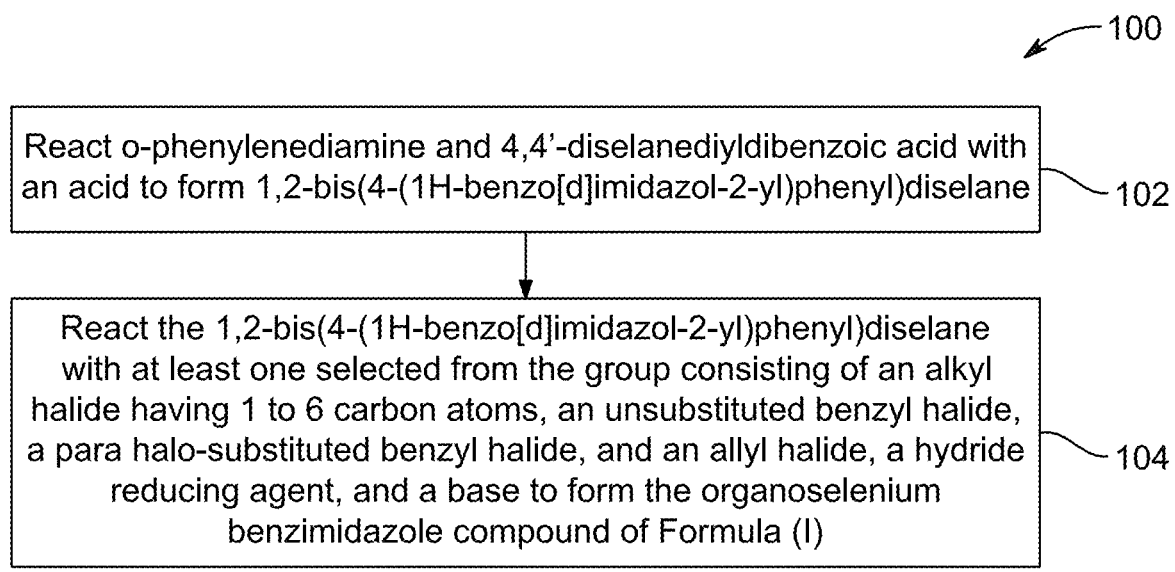
FIG. 1 is a flowchart depicting the synthesis of organoselenium benzimidazole compounds, according to certain embodiments.

In the drawings, reference numerals designate identical or corresponding parts throughout the several views. Further, as used herein, the words "a," "an," and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

As used herein, the term 'cancer' refers to all types of cancer, neoplasm, or malignant tumors found in mammals (e.g., humans), including leukemias, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

An "anticancer agent" or "anticancer compound" as used herein refers to a molecule (e.g., compound, peptide, protein, nucleic acid, 0103) used to treat cancer through the destruction or inhibition of cancer cells or tissues. Anticancer agents may be selective for certain cancers or specific tissues.

As used herein, "analogue" refers to a chemical compound that is structurally similar to a parent compound, but differs slightly in composition (e.g., one atom or functional group is different, added, or removed). The analogue may or may not have chemical or physical properties different from the original compound and may or may not have improved biological and/or chemical activity. For example, the analogue may be more hydrophilic, or it may have altered reactivity as compared to the parent compound. The analogue may mimic the chemical and/or biologically active of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic, or it may have altered reactivity as compared to the parent compound. Derivatization (i.e., modification) may involve the substitution of one or more moieties within the molecule (e.g., a change in a functional group). The term "derivative" also includes conjugates, and prodrugs of a parent compound (i.e., chemically modified derivatives that can be converted into the original compound under physiological conditions).

The term "therapeutically effective amount" as used herein refers to the amount of the complex being administered which will relieve to some extent one or more of the symptoms of the disorder being treated. In reference to cancer or pathologies related to increased cell division, a therapeutically effective amount refers to that amount which has the effect of at least one of the following: (1) reducing the size of a tumor, (2) inhibiting (that is, slowing to some extent, preferably stopping) aberrant cell division, growth or proliferation, for example, cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s), and/or complexes that can be used in the prevention, treatment and/or management of a cancer or one or more symptoms thereof.

As used herein, the terms "treat," "treatment," and "treating" in the context of the administration of a therapy to a subject in need thereof refer to the reduction or inhibition of the progression and or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in cancer stem cell population. In some embodiments, such terms refer to a stabilization or reduction in the growth of cancer cells. In some embodiments, such terms refer to stabilization or reduction in the cancer stem cell population and a reduction in the cancer cell population. In some embodiments, such terms refer to a stabilization or reduction in the growth and or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in the survival rate of a patient population. In further embodiments, such terms refer to an increase in the response rate, the durability of response, or the number of patients who respond or are in remission. In some embodiments, such terms refer to a decrease in the hospitalization rate of a patient population and/or a decrease in hospitalization length for a patient population.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g., mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e.g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

A "pharmaceutical composition" refers to a mixture of the compounds described herein or pharmaceutically acceptable salts, esters, or prodrugs thereof, with other chemical components, such as physiologically acceptable carriers and excipients.

As used herein, the terms "pharmaceutically acceptable salt" or "pharmaceutically acceptable ester" refer to a compound in a pharmaceutically acceptable form such as an ester, a phosphate ester, a salt of an ester, or a related) which, upon administration to a subject in need thereof, provides a compound of Formula (I) as described herein. Pharmaceutically acceptable salts and esters retain the biological effectiveness and properties of the free bases, which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Suitable salts include those derived from alkali metals such as potassium and sodium, and alkaline earth metals such as calcium and magnesium, among numerous other acids well-known in the art.

As used herein, a "pharmaceutically acceptable carrier" refers to a carrier or diluent that does not cause significant irritation to an organism and does not abrogate the biological activity and properties of the administered compound of Formula (I). The term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

"Alkyl" refers to monovalent saturated aliphatic hydrocarbyl groups having from 1 to 10 carbon atoms and such as 1 to 6 carbon atoms, or 1 to 5, or 1 to 4, or 1 to 3, or 1 to 2 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (t-Bu)(($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 10 substituents selected from the group consisting of deuterium, alkoxy, substituted alkoxy, cycloalkyl, substituted cycloalkyl, cycloalkenyl, substituted cycloalkenyl, alkylaminoalkyl, alkylaminoalkenyl, alkylaminoalkynyl, haloalkoxy, haloalkyl, alkylalkoxy, alkylthioalkoxy, acyl, acylamino, acyloxy, amino, aminoacyl, aminoacyloxy, aminosulfonyl, sulfonylamino, oxyaminoacyl, azido, cyano, halogen, hydroxyl, oxo, sulfonyl, sulfonyloxy, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR'R", wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups having from 1 to 6, including, for example, 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups-alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group-NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups-alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group-alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms, for example 2 to 4 carbon atoms and having at least 1, for example from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms, for example, 2 to 3 carbon atoms and having at least 1 and for example, from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from deuterium, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, and —SO$_2$-heteroaryl.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)

"Acylamino" refers to the groups —NR$^{20}$C(O) alkyl, —NR$^{20}$C(O)substituted alkyl, N —R$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O) alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group-O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclohexyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from deuterium, alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and for example, from 1 to 2 double bonds.

The term "substituted cycloalkenyl" refers to cycloalkenyl groups having from 1 to 5 substituents, or from 1 to 3 substituents, selected from deuterium, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups-alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, benzo[d][1,3]oxathiole, benzo[d][1,3]dioxole, and the like.

Unless otherwise constrained by the definition for the heterocyclic substituent, such heterocyclic groups can be optionally substituted with 1 to 5, or from 1 to 3 substituents, selected from deuterium, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

An "excipient" refers to an inert substance added to a pharmaceutical composition to facilitate the administration of a compound. Examples, without limitation, of excipients include calcium carbonate, calcium phosphate, various sugars and types of starch, cellulose derivatives, gelatin, vegetable oils, and polyethylene glycols.

As used herein, the terms "the patient", "subject", and "individual" are used interchangeably. As used herein, they refer to individuals suffering from a disease and encompass mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In preferred embodiments, the subject is a human.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), intravaginal administration, and rectal administration. Those of ordinary skill in the art are familiar with administration techniques that can be employed with the compounds and methods described herein. In preferred embodiments, the active ingredient and/or the pharmaceutical composition described herein are administered orally.

As used herein, the term 'oral administration' refers to the most common routes of drug administration, where medications are taken by mouth and absorbed through the gastrointestinal tract. Oral medications can include tablets, capsules, syrups, or suspensions. They are convenient for patients and are often self-administered. However, oral medications may be subject to degradation in the gastrointestinal tract and may have variable absorption rates depending on factors such as gastric emptying and gastrointestinal pH.

As used herein, the term 'parenteral administration' refers to the route involving delivering medications directly into the body, bypassing the gastrointestinal tract. Parenteral administration can be achieved through various routes, including intravenous (IV), intramuscular (IM), subcutaneous (SC), or intradermal (ID) injection. These routes allow for rapid onset of action and precise control over drug delivery. Parenteral administration is often used for medications that require immediate effects, have poor oral bioavailability, or need to bypass the gastrointestinal tract due to issues such as nausea or vomiting.

As used herein, the term 'rectal administration' refers to administering medications by inserting them into the rectum using suppositories, enemas, or rectal solutions. This route is particularly useful for patients who cannot take medications orally or require local or systemic drug absorption. Rectal administration can provide rapid absorption and avoid issues associated with oral administration, such as first-pass metabolism. Common medications administered rectally include treatments for constipation, hemorrhoids, and inflammatory bowel disease.

Topical medications are applied directly to the skin or mucous membranes for localized or systemic effects. This route is commonly used for dermatological conditions, wound healing, pain management, and local anesthesia. Topical formulations include creams, ointments, gels, lotions, patches, and sprays. Topical administration allows for targeted drug delivery to specific areas while minimizing systemic side effects.

Transdermal delivery involves applying medications to the skin for systemic absorption. Unlike topical administration, transdermal medications are designed to penetrate the skin and enter the bloodstream, providing sustained drug release over an extended period. Transdermal patches are a common form of transdermal delivery and are used for medications such as hormonal contraceptives, nicotine replacement therapy, and pain management.

Intralesional administration involves injecting medications directly into a specific lesion or localized area, such as a tumor, cyst, or inflamed tissue. These injections allow for targeted delivery of medications to the site of action, minimizing systemic exposure and side effects. This route is commonly used in dermatology, oncology, and rheumatology to treat skin disorders, cancerous lesions, and joint inflammation.

Inhalation administration involves delivering medications directly into the respiratory tract for local or systemic effects. This route can be achieved through various devices such as metered-dose inhalers, dry powder inhalers, nebulizers, or vaporizers. It is commonly used for treating respiratory conditions such as asthma, chronic obstructive pulmonary disease (COPD), and respiratory infections. Inhalation allows for rapid absorption of medications into the lungs and bloodstream, resulting in quick onset of action and reduced systemic side effects.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}$C and $^{14}$C. Isotopes of selenium include $^{72}$Se, $^{74}$Se, $^{75}$Se, $^{77}$Se, $^{78}$Se, $^{79}$Se, $^{80}$Se, and $^{82}$Se. Isotopically labeled compounds of the disclosure can generally be prepared by conventional techniques known to those skilled in the art or by processes and methods analogous to those described herein, using an appropriate isotopically-labeled reagent in place of the non-labeled reagent otherwise employed.

According to the first aspect, the present disclosure is related to a method of treating cancer in a subject in need thereof. In general, the cancer can be any suitable type of cancer. In some embodiments, the cancer is at least one selected from the group consisting of glioblastoma, colorectal cancer, lung cancer, head and neck cancer, gastric cancer, pancreatic cancer, breast cancer, ovarian cancer, hepatocellular carcinoma, renal cell cancer, liver cancer, B-cell lymphoma, and cervical cancer.

In some embodiments, the method includes administering a therapeutically effective amount of an organoselenium benzimidazole compound of Formula (I) to the subject, wherein:

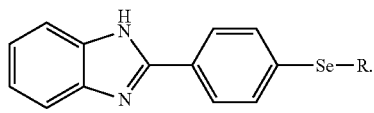
(I)

In Formula (I), R can in general be any carbon-containing group. Examples of carbon-containing groups are included above. In some embodiments, R can be any of an alkyl group having 1 to 10 carbon atoms, an alkenyl group, an alkynyl group, an aryl group, an aralkyl group, and a cyano group. In general, the carbon-containing group can be unsubstituted or substituted as described above. In some embodiments, the alkyl group can be a cycloalkyl group. In some embodiments, the alkyl group has 1 to 6 carbon atoms. In some embodiments, the alkyl group has 1 to 3 carbon atoms. In some embodiments, the alkyl group is at least one selected from the group consisting of methyl, ethyl, and n-propyl.

In some embodiments, the alkenyl group has 2 to 6 carbon atoms. In some embodiments, the alkenyl group has 2 to 3 carbon atoms. In some embodiments, the alkenyl group is allyl.

In some embodiments, the aralkyl group is a benzyl group. In some embodiments, the benzyl group includes an unsubstituted benzene moiety. Such a group may be referred to as an "unsubstituted benzyl group". In some embodiments, the benzyl group includes a substituted benzene moiety. Such a group may be referred to as an "substituted benzyl group". In some embodiments, the substituted benzene moiety includes is a halo-substitute benzene moiety. In some embodiments, the substituted benzene moiety includes is a para halo-substitute benzene moiety. Such a group may be referred to as a "para halo-substituted benzyl group".

In some embodiments, the organoselenium benzimidazole compound of Formula (I) is at least one selected from Formulae (II) to (VII)

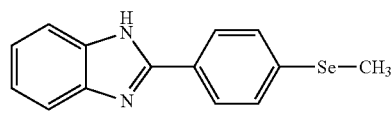
(II)

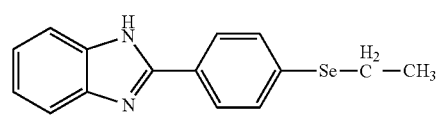
(III)

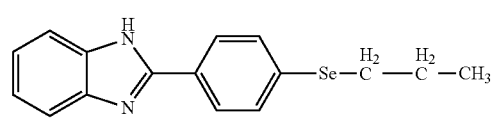
(IV)

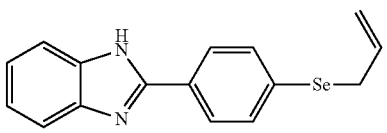
(V)

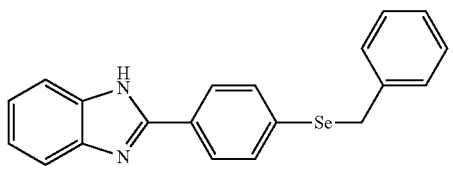
(VI)

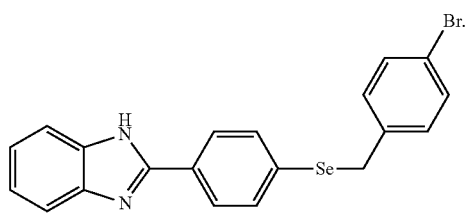
(VII)

In some embodiments, the organoselenium benzimidazole compound of Formula (I) has a mechanism of action that inhibits GPX4. In some embodiments, the organoselenium benzimidazole compound of Formula (I) has a mechanism of action that includes binding to GPX4 with a binding affinity of −5.50 to −4.25 kcal/mol. GPX4 (Glutathione Peroxidase 4) typically acts as a negative regulator of ferroptosis, a form of regulated cell death driven by lipid peroxidation. Inhibition of GPX4, for example, by a organoselenium benzimidazole compound of Formula (I), may cause cell death by including ferroptosis. In some embodiments, organoselenium benzimidazole compound forms a 1:1 molar complex with glutathione peroxidase 4 (GPX4).

The present disclosure also relates to a pharmaceutical composition including the compound of Formula (I) or a pharmaceutically acceptable salt thereof. In some embodiments, the pharmaceutical composition further includes a pharmaceutically acceptable carrier and/or excipient. In some embodiments, the pharmaceutical composition includes a pharmaceutically acceptable carrier and/or excipient is at least one of a buffer, an inorganic salt, a synthetic fatty acid, a vegetable oil, a fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 34(3-cholamidopropyl) dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltriniethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly (malic acid), poly (maleic anhydride), a polyvinyl alcohols, and copolymers, terpolymers, or combinations or mixtures therein. The copolymer/terpolymer may be a random copolymer/terpolymer, or a block copolymer/terpolymer.

In some embodiments, the pharmaceutical composition includes one or more of a sweetener, a flavoring, and a colorant.

In some embodiments, therapeutically effective amount of the compound of Formula (I) or a pharmaceutically acceptable salt thereof is from 0.1 milligrams per kilogram of body weight of the subject (mg/kg) to 1000 mg/kg, preferably 0.25 mg/kg to 975 mg/kg, preferably 0.5 mg/kg to 950 mg/kg, preferably 0.75 mg/kg to 925 mg/kg, preferably 1 mg/kg to 900 mg/kg, preferably 1.25 mg/kg to 875 mg/kg, preferably 1.5 mg/kg to 850 mg/kg, preferably 1.75 mg/kg to 825 mg/kg, preferably 2.0 to 800 mg/kg, preferably 2.25 mg/kg to 775 mg/kg, preferably 2.5 mg/kg to 750 mg/kg. In some embodiments, the therapeutically effective amount of the compound of formula (I) or a pharmaceutically acceptable salt thereof, is from 5 mg/kg to 500 mg/kg, preferably 7.5 mg/kg to 450 mg/kg, preferably 10 mg/kg to 400 mg/kg, preferably 15 mg/kg to 350 mg/kg, preferably 20 mg/kg to 300 mg/kg, preferably 25 mg/kg to 250 mg/kg. An appropriate therapeutically effective amount may differ from one individual to another. An appropriate therapeutically effective amount in any individual case may be determined using techniques, such as a dose escalation study.

The dosage and treatment duration is dependent on factors such as the bioavailability of a drug, administration mode, toxicity of a drug, gender, age, lifestyle, body weight, the use of other drugs and dietary supplements, cancer stage, tolerance, and resistance of the body to the administered drug, etc., then determined and adjusted accordingly.

In general, an amount of Formula (I) compound that can be combined with the pharmaceutically acceptable carrier and/or excipients to produce a single dosage form varies depending upon the mammalian subject treated and the particular mode of administration. The dosage and treatment duration are dependent on factors, such as the bioavailability of a drug, administration mode, toxicity of a drug, gender, age, lifestyle, body weight, the use of other drugs and dietary supplements, the disease stage, tolerance, and resistance of the body to the administered drug, etc., and then determined and adjusted accordingly.

In general, the compound of Formula (I) or a pharmaceutical composition thereof may be administered in a single dose or multiple individual divided doses. In some embodiments, the interval of time between the administration of the compound of Formula (I) or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks. 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period in between. In certain embodiments, the compound of Formula (I) and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the compound of Formula (I) or a pharmaceutical composition containing it may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cisplatin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguaniue), tipifarnib. Examples of antineoplastic agents which are protein kinase inhibitors include imatinib, erlotinib, sorafenib, sunitinib, dasatinib, nilotinib, lapatinib, gefitinib, temsirolimus, everolimus, rapamycin, bosutinib, pazopanib, axitinib, neratinib, vatalanib, pazopanib, midostaurin, and enzastaurin. Examples of antineoplastic agents which are antibodies comprise trastuzumab, cetuximab, panitumumab, rituximab, bevacizumab, mapatumumab, conatumumab, lexatumumab, and the like.

In some embodiments, the pharmaceutical composition is formulated for at least one mode of administration, which may be oral, parenteral, rectal, topical, transdermal, intralesional, or inhalation administration, containing conventional non-toxic pharmaceutically acceptable carriers, adjuvants, and vehicles as desired.

Topical administration can also involve the use of transdermal administration, such as transdermal patches or iontophoresis devices. The term parenteral, as used herein, includes intravesical, intradermal, transdermal, subcutaneous, intramuscular, intralesional, intracranial, intrapulmonary, intracardial, intrasternal, and sublingual injections, or infusion techniques. Formulation of drugs is discussed in, for example, Hoover, John E., Remington's Pharmaceutical Sciences, Mack Publishing Co., Easton, Pa.; 1975. Another example includes Liberman, H. A. and Lachman, L., Eds., Pharmaceutical Dosage Forms, Marcel Decker, New York, N.Y., 1980, which is incorporated herein by reference in its entirety.

Injectable preparations, for example, sterile injectable aqueous or oleaginous suspensions, can be Formulated according to the known art using suitable dispersing or wetting agents and suspending agents. The sterile injectable preparation can also be a sterile injectable solution or suspension in a nontoxic, parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any fixed oil can be employed, including synthetic mono- or diglycerides. In addition, fatty acids such as oleic acid are used in the preparation of injectables. Dimethyl acetamide, surfactants including ionic and non-ionic detergents, and polyethylene glycols can be used. Mixtures of solvents and wetting agents, such as those discussed above, are also useful. Suppositories for rectal administration of the compound or an analogue or derivative thereof can be prepared by mixing the steroid or an analogue or derivative thereof with a suitable non-irritating excipient such as cocoa butter, synthetic mono- di- or triglycerides, fatty acids, and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered per os, a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the active compound in hydroxypropyl methylcellulose. In the case of capsules, tablets, and pills, the dosage forms can also comprise buffering agents such as sodium citrate, magnesium or calcium carbonate, or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending, agents, sweetening, flavoring, and perfuming agents.

The methods for treating cancer and other proliferative disorders described herein inhibit, remove, eradicate, reduce, regress, diminish, arrest, or stabilize a cancerous tumor, including at least one of the tumor growth, tumor cell viability, tumor cell division, and proliferation, tumor metabolism, blood flow to the tumor and metastasis of the tumor. In some embodiments, after treatment with the compound of Formula (I) or a pharmaceutical composition thereof, the size of a tumor, whether by volume, weight, or diameter, is reduced by at least 5%, 10%, 15%, 20%, 25%, 30%, 40%, 50%, 60%, 70%, 75%, relative to the tumor size before treatment. In other embodiments, after treatment with the compound of Formula (I) or a pharmaceutical composition thereof, the size of a tumor does not reduce but is maintained the same as the tumor size before treatment. Methods of assessing tumor size include but are not limited to CT scan, MRI, DCE-MRI, and PET Scan.

FIG. 1 illustrates a schematic flow chart of a method 100 of organoselenium benzimidazole compound of the Formula (I). The order in which the method 100 is described is not intended to be construed as a limitation, and any number of the described steps can be combined in any order to implement the process 100. Additionally, individual steps may be removed or skipped from the process 100 without departing from the spirit and scope of the present disclosure.

At step 102, the method 100 includes reacting o-phenylenediamine and 4,4'-diselanediyldibenzoic acid with an acid to form 1,2-bis(4-(1H-benzo[d]imidazol-2-yl)phenyl)diselane. In some embodiments, the acid includes acetic acid, polyphosphoric acid, and water. In some embodiments, the acid is acetic acid. In some embodiments, the reaction is performed at 160 to 200° C., preferably 180° C. for a sufficient period of time. In some embodiments, the reacting is performed under stirring.

At step 104, the method 100 includes reacting the 1,2-bis(4-(1H-benzo[d]imidazol-2-yl)phenyl)diselane with at a halide-substituted carbon-containing reagent, a hydride reducing agent, and a base to form the organoselenium benzimidazole compound of Formula (1). In general, the halide-substituted carbon-containing reagent can be any suitable reagent containing a carbon-halogen bond. As depicted by the schemes herein, the halide-substituted carbon-containing reagent becomes the R group in Formula (I). As such, in some embodiments, the halide-substituted carbon-containing reagent is X—R where R is defined as above and X is a halogen atom. In some embodiments, the halide-substituted carbon-containing reagent is at least one selected from the group of an alkyl halide having 1 to 6 carbon atoms, an unsubstituted benzyl halide, a para halo-substituted benzyl halide, and an allyl halide, some embodiments, the alkyl group, which has 1 to 3 carbon atoms, is at least one selected from the methyl, ethyl, and n-propyl.

In some embodiments, the hydride reducing agent is at least one of lithium aluminum hydride, sodium borohydride, diisobutylaluminum hydride, sodium cyanoborohydride, and/or mixtures thereof. In some embodiments, the hydride reducing agent is sodium borohydride.

In some embodiments, the base is an alkali metal hydroxide. Suitable examples of alkali metal hydroxide include, but are not limited to, sodium hydroxide, potassium hydroxide, lithium hydroxide, rubidium hydroxide, cesium hydroxide, etc. In some embodiments, the alkali metal hydroxide is NaOH.

In some embodiments, the molar ratio of the alkyl halide to the hydride reducing agent is about 1:5 to 5:1, preferably 1:4 to 4:1, preferably 1:3 to 3:1, preferably 1:2 to 2:1, preferably about 1:1.2.

In some embodiments, the reaction mixture is stirred for 1 to 10 hours, preferably for 2-8 hours, preferably for 4-6 hours, preferably 4 hours, to obtain the compound of Formula (I).

EXAMPLES

The following examples demonstrate a method of treating cancer using organoselenium-based benzimidazoles as described herein. The examples are provided solely for illustration and are not to be construed as limitations of the present disclosure, as many variations thereof are possible without departing from the spirit and scope of the present disclosure.

Example 1: Synthesis of Organoselenium benzimidazoles

Figure 2A:
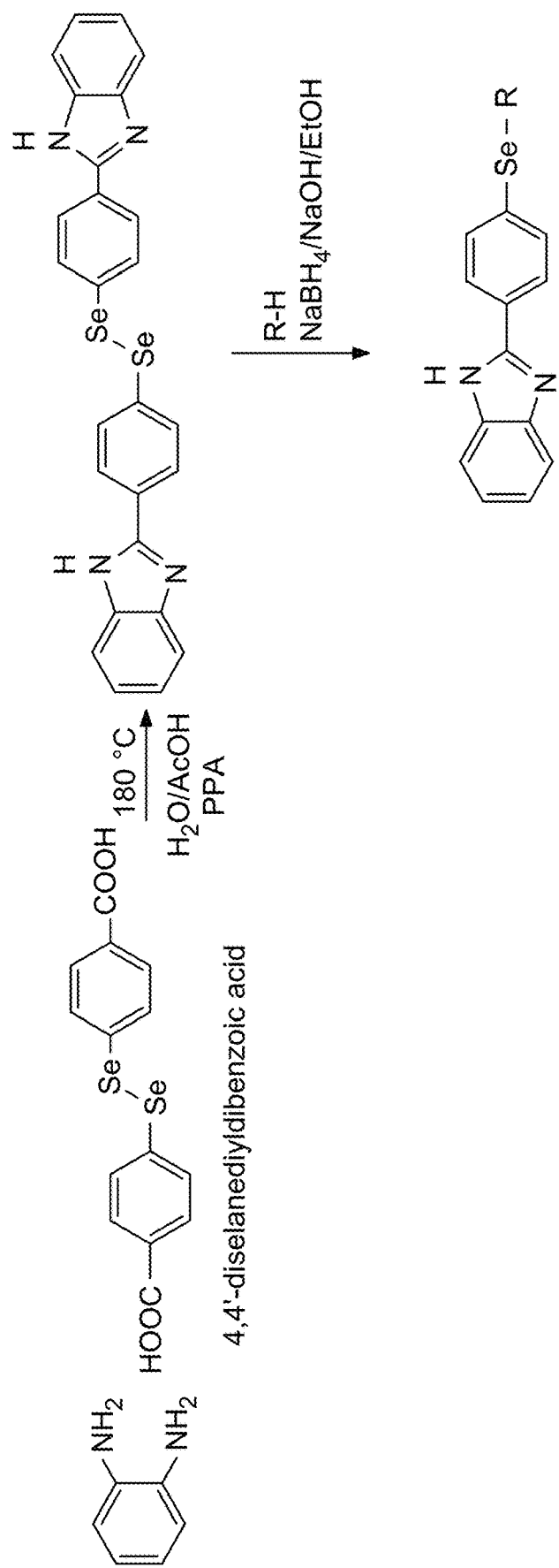
FIG. 2A is a schematic illustration depicting the synthesis of organoselenium benzimidazole compounds, according to certain embodiments.
Figure 2B:
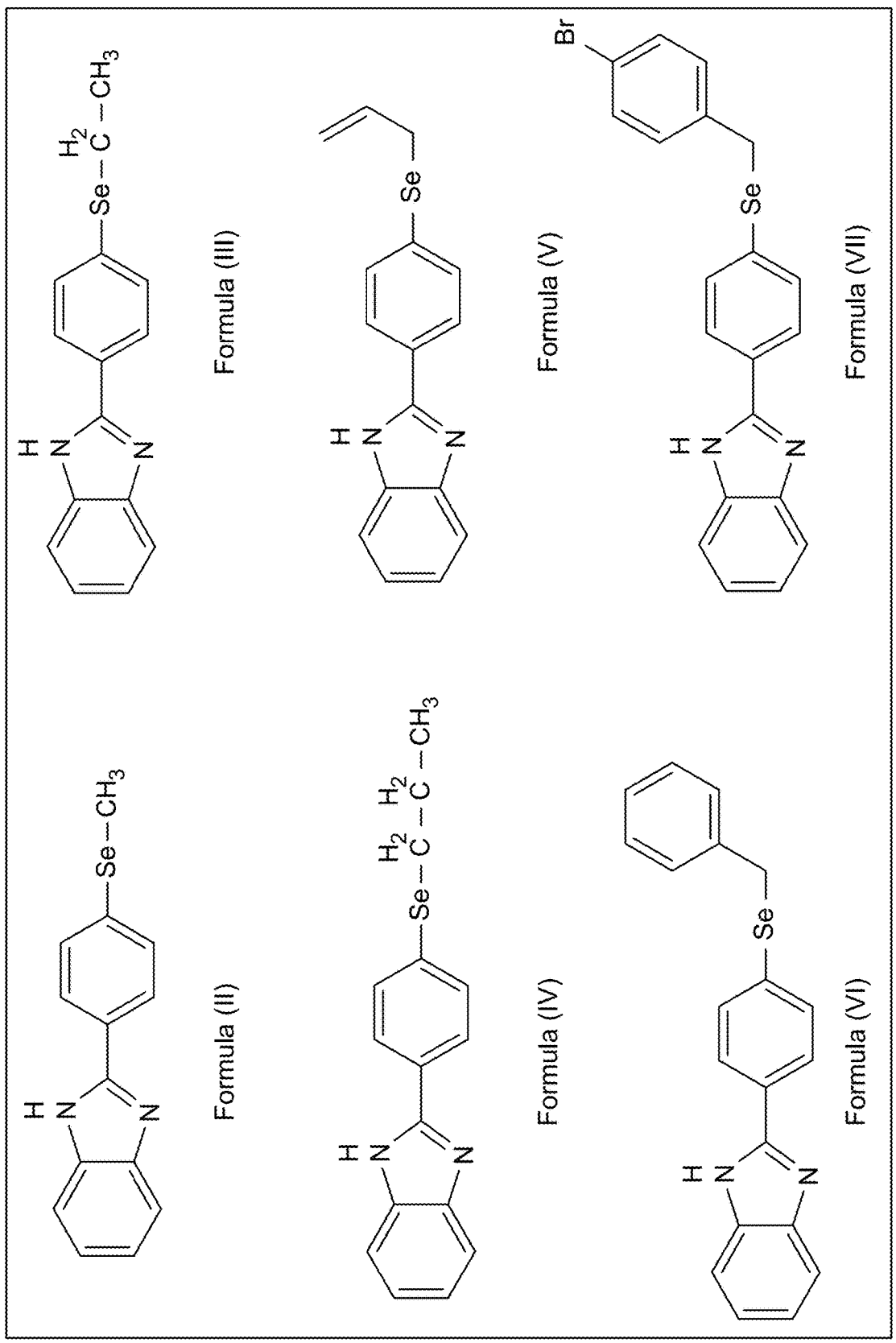
FIG. 2B shows 3D structures of various organoselenium benzimidazole compounds, according to certain embodiments.
Figure 3A:
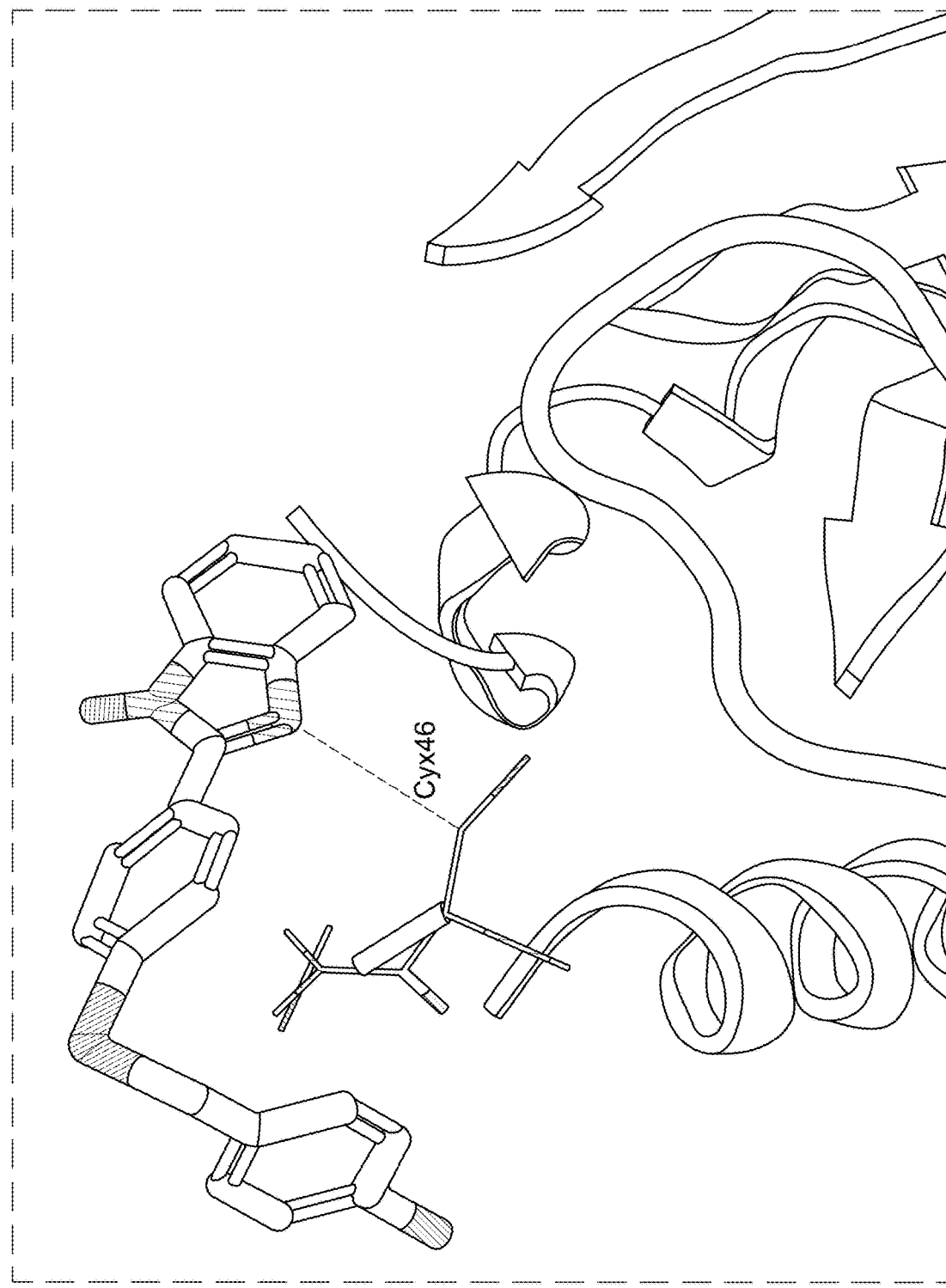
FIG. 3A-FIG. 3D is an exemplary illustration depicting the 3D binding interactions and positioning of compound VII and the co-crystallized inhibitor of the glutathione peroxidase 4 (GPX4) (PDB ID: 6HKQ), according to certain embodiments.
Figure 3B:
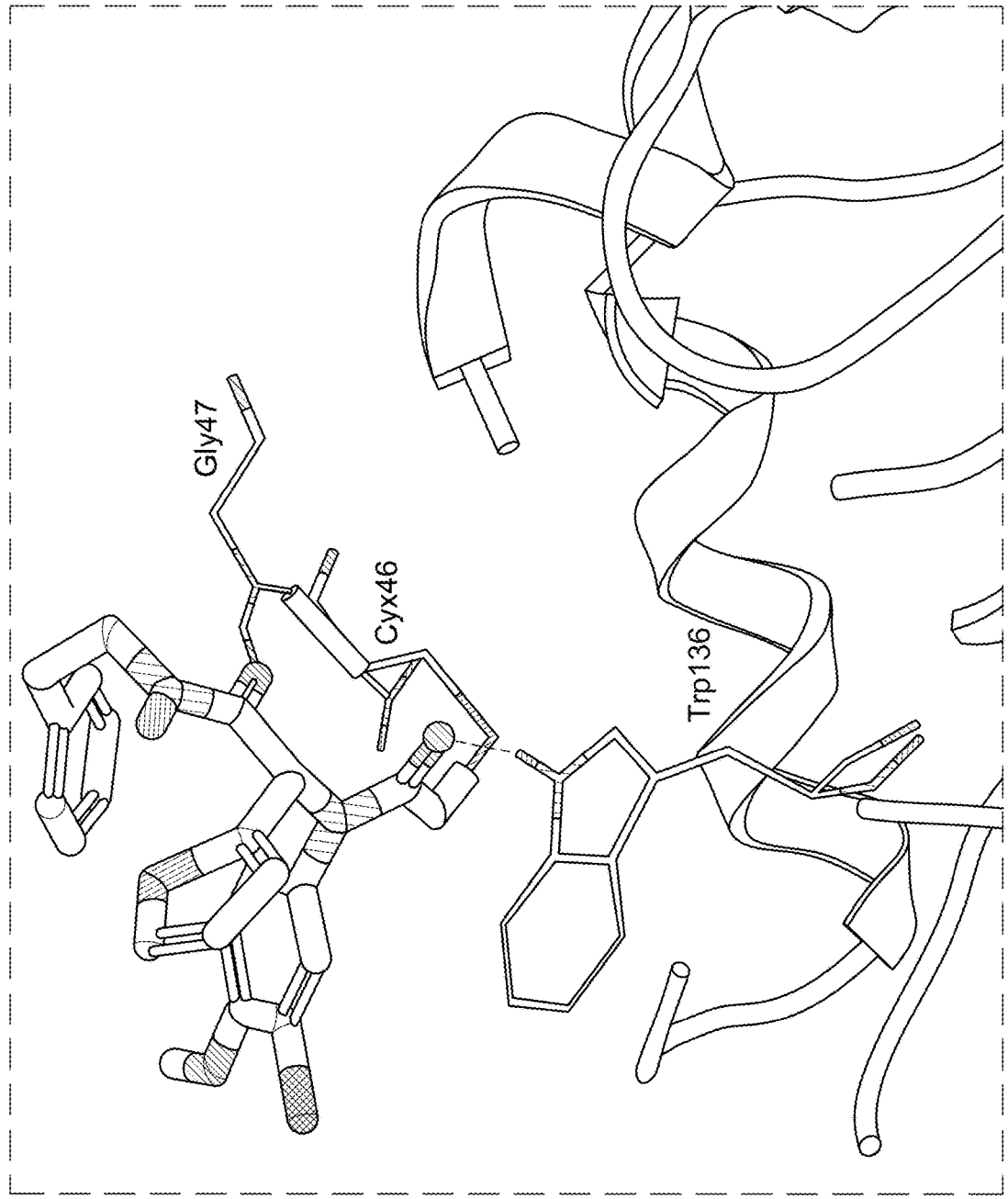
Figure 3C:
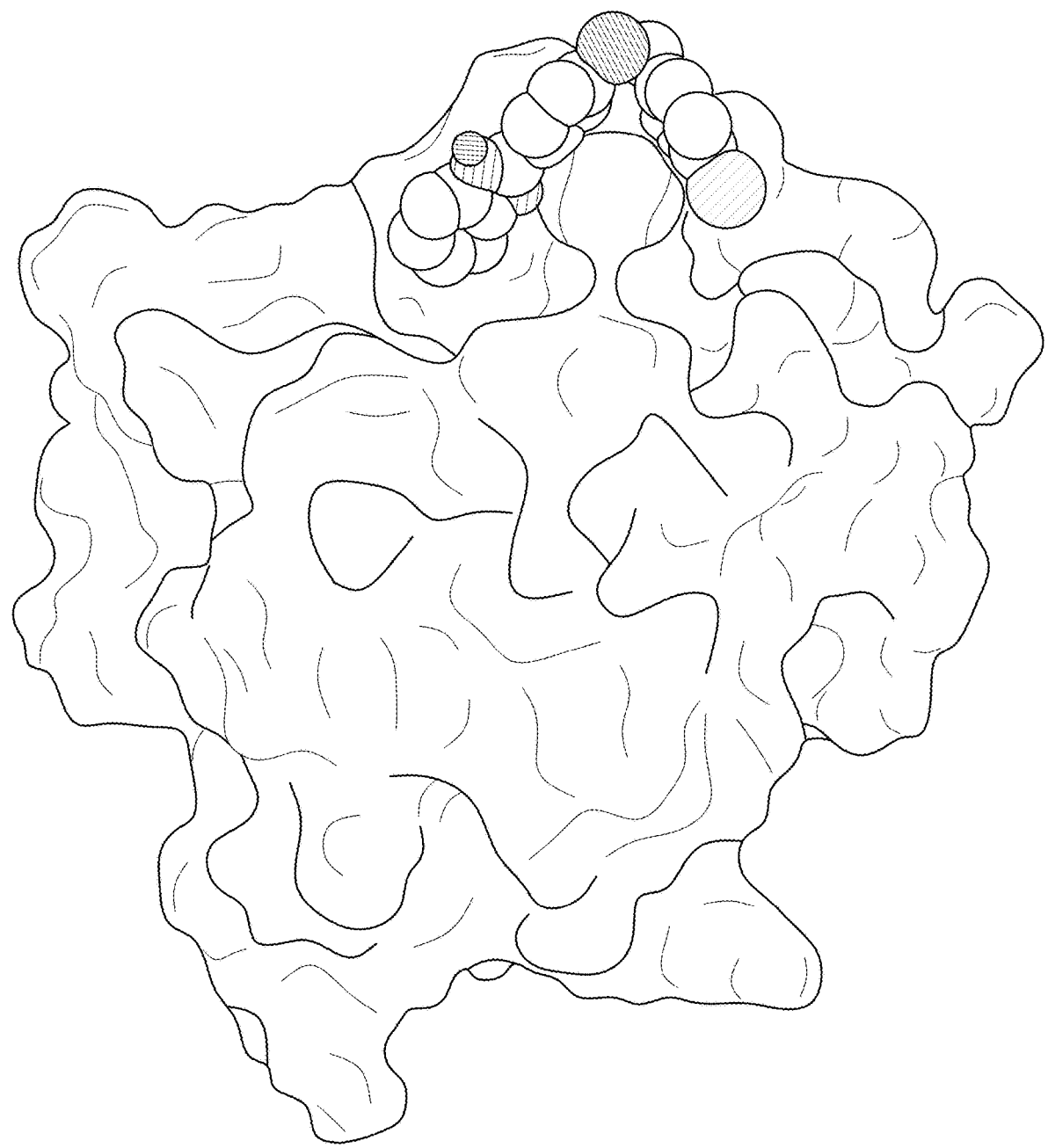
Figure 3D:
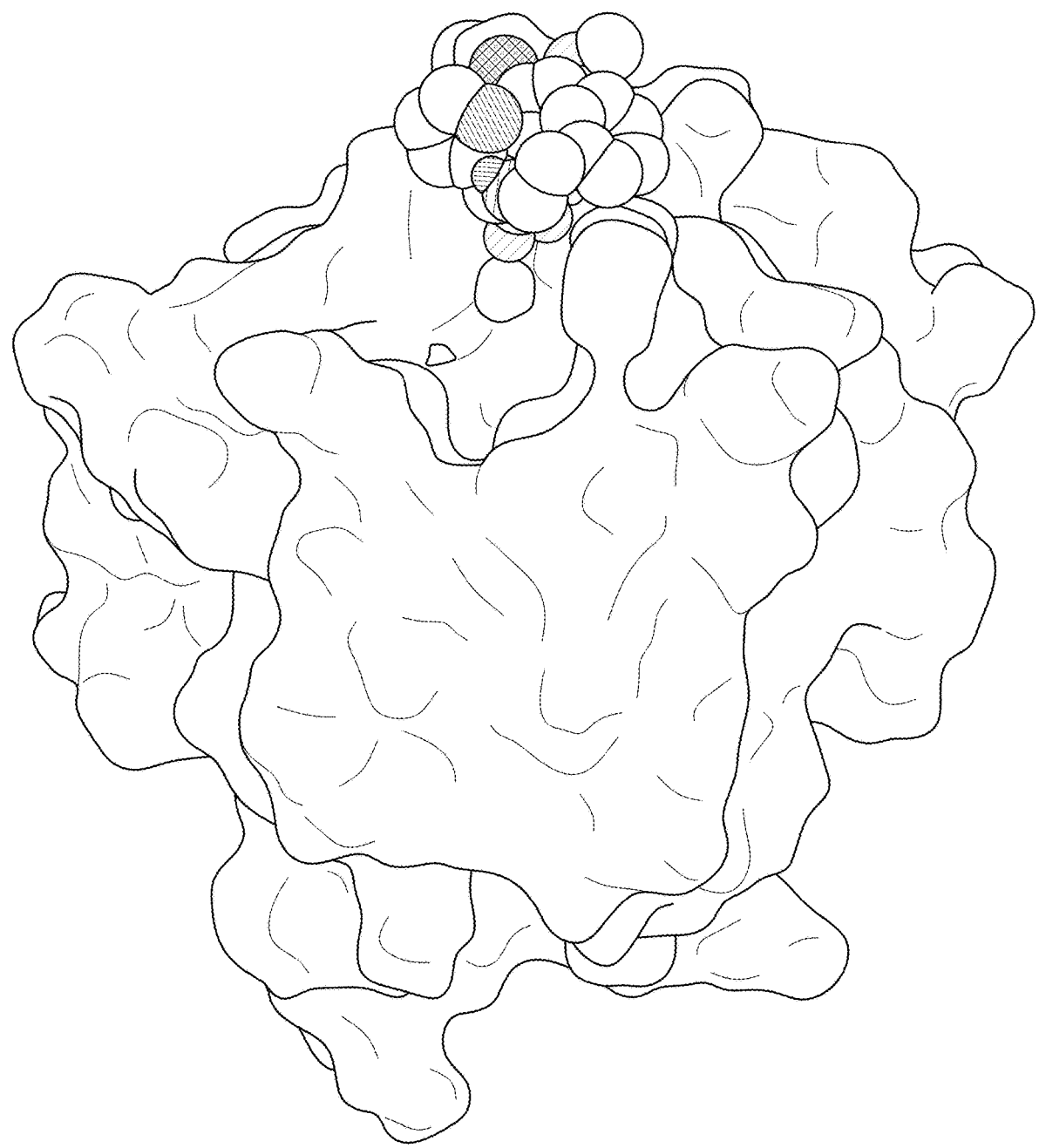

Organoselenium benzimidazoles (Formula II to Formula VII) were synthesized by the reduction of 1,2-bis(4-(1H-benzo[d]imidazol-2-yl)phenyl)diselane (3) using NaBH$_4$ and NaOH in ethanol. In brief, 1,2-bis(4-(1H-benzo[d]imidazol-2-yl)phenyl)diselane (3) (1 mmol) was suspended in ethanol (30 ml) containing NaOH (1 mmol). Alkyl halide (2.2 mmol) and NaBH$_4$ (2.5 mmol) were then added to the mixture and stirred for 4 h. The progress of the reaction was followed by TLC; after completion, the reaction was quenched by adding water and extracted by ethyl acetate. The organic layer was dried over Na$_2$SO$_4$ and dried under a vacuum to give organoselenium-based benzimidazoles (Formula II to Formula VII). A schematic illustration depicting the synthesis of organoselenium benzimidazole compounds is illustrated in FIG. 2A, and the 3D structures of compounds of Formula II to Formula VII is depicted in FIG. 2B.

Example 2: Synthesis of 2-(4-(methylselanyl)phenyl)-1H-benzo[d]imidazole (Formula II)

Formula II was synthesized from the reaction of 1,2-bis(4-(1H-benzo[d]imidazol-2-yl)phenyl)diselane (3) (1 mmol) with methyl iodide (2.2 mmol), NaBH$_4$ (2.5 mmol), and NaOH (1 mmol) in ethanol (30 ml).

Example 3: Synthesis of 2-(4-(ethylselanyl)phenyl)-1H-benzo[d]imidazole (Formula III)

Formula III was synthesized from the reaction of 1,2-bis(4-(1H-benzo[d]imidazol-2-yl)phenyl)diselane (3) (1 mmol) with ethyl iodide (2.2 mmol), NaBH$_4$ (2.5 mmol), and NaOH (1 mmol) in ethanol (30 ml).

Example 4: Synthesis of 2-(4-(propylselanyl)phenyl)-1H-benzo[d]imidazole (Formula IV)

Formula IV was synthesized from the reaction of 1,2-bis(4-(1H-benzo[d]imidazol-2-yl)phenyl)diselane (3) (1 mmol) with propyl chloride (2.2 mmol), NaBH$_4$ (2.5 mmol), and NaOH (1 mmol) in ethanol (30 ml).

Example 5: Synthesis of 2-(4-(allylselanyl)phenyl)-1H-benzo[d]imidazole (Formula V)

Formula V was synthesized from the reaction of 1,2-bis(4-(1H-benzo[d]imidazol-2-yl)phenyl)diselane (3) (1 mmol) with allyl chloride (2.2 mmol), NaBH$_4$ (2.5 mmol), and NaOH (1 mmol) in ethanol (30 ml).

Example 6: Synthesis of 2-(4-(benzylselanyl)phenyl)-1H-benzo[d]imidazole (Formula VI)

Formula VI was synthesized from the reaction of 1,2-bis(4-(1H-benzo[d]imidazol-2-yl)phenyl)diselane (3) (1 mmol) with benzyl chloride (2.2 mmol), NaBH$_4$ (2.5 mmol), and NaOH (1 mmol) in ethanol (30 ml).

Example 7: 2-(4-((4-bromobenzyl) selanyl)phenyl)-1H-benzo[d]imidazole (Formula VII)

Formula VII was synthesized from the reaction of 1,2-bis(4-(1H-benzo[d]imidazol-2-yl)phenyl)diselane (3) (1 mmol) with 1-bromo-4-(bromomethyl)benzene (2.2 mmol), NaBH$_4$ (2.5 mmol), and NaOH (1 mmol) in ethanol (30 ml).

Example 8: Docking Studies

The docking properties of the compounds of Formula II-VII towards the binding site of the glutathione peroxidase 4 (GPX4) (PDB ID: 6HKQ) were investigated. Their binding scores were reported to be −4.51, −4.68, −4.98, −4.97, −5.12, and −5.33 kcal/mol, respectively, compared to the docked co-crystallized inhibitor (−5.40 kcal/mol). Notably, the compound of Formula VII was found to be a promising candidate with a binding score comparable to that of the co-crystallized inhibitor. This may be attributed to its elongated side chain (p-bromophenyl moiety), which extended more to fill the external pocket of the GPX4, as clarified from the 3D binding orientation and positioning docking view (FIG. 3A-FIG. 3D). The binding mode of compound of Formula VII showed the formation of one hydrogen bond with Cyx46 which is an important amino acid responsible for the inhibitory potential towards the GPX4 receptor. This was clear from the binding interaction of the co-crystallized inhibitor, which bound Cyx46 covalently and formed two extra hydrogen bonds with Gly47 and Trp136 amino acids as well (FIG. 3A-FIG. 3D). The greatly similar binding score of compound of Formula VII to that of the co-crystallized covalent inhibitor of the GPX4 receptor with stronger and more potent binding interactions confirms its greater binding affinity.

Numerous modifications and variations of the present disclosure are possible in light of the above teachings. It is, therefore, to be understood that within the scope of the appended claims, the invention may be practiced otherwise than as specifically described herein.

The invention claimed is:

1. A method of treating cancer in a subject in need thereof, the method comprising administering a therapeutically effective amount of an organoselenium benzimidazole compound of formula (I),

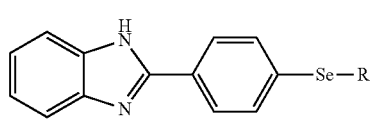
(I)

to the subject, wherein
R is at least one selected from the group consisting of an alkyl group having 1 to 6 carbon atoms, an unsubstituted benzyl group, a para halo-substituted benzyl group, and an allyl group.

2. The method of claim 1, wherein the alkyl group having 1 to 6 carbon atoms is at least one selected from the group consisting of methyl, ethyl, and n-propyl.

3. The method of claim 1, wherein the organoselenium benzimidazole compound of formula (I) is at least one selected from formulae (II) to (VII)

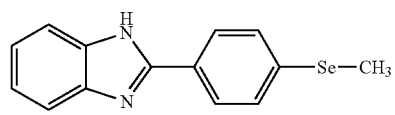
(II)

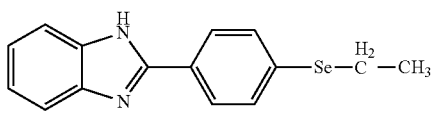
(III)

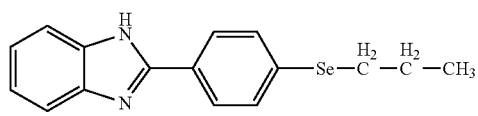
(IV)

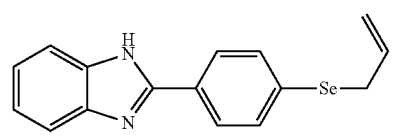
(V)

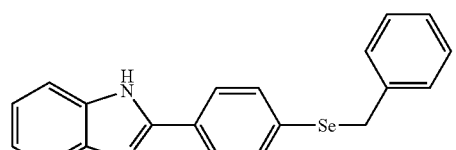
(VI)

(VII)

4. The method of claim 1, wherein the cancer is at least one selected from the group consisting of glioblastoma, colorectal cancer, lung cancer, head and neck cancer, gastric cancer, pancreatic cancer, breast cancer, ovarian cancer, hepatocellular carcinoma, renal cell cancer, liver cancer, B-cell lymphoma, and cervical cancer, and
wherein the organoselenium benzimidazole compound has formula (VII)

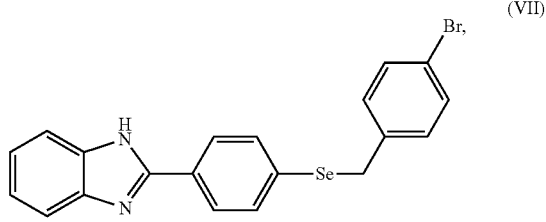 [SMILES: Brc1ccc(C[Se]c2ccc(-c3nc4ccccc4[nH]3)cc2)cc1]
(VII)

and
the administering forms a 1:1 molar complex comprising the organoselenium benzimidazole compound and glutathione peroxidase 4.

5. The method of claim 1, wherein the organoselenium benzimidazole compound of formula (I) has a mechanism of action that includes inhibition of GPX4.

6. The method of claim 5, wherein the organoselenium benzimidazole compound of formula (I) acts to inhibit GPX4 by binding to GPX4 with a binding affinity of −5.50 to −4.25 kcal/mol.

7. The method of claim 5, wherein the inhibition of GPX4 causes ferroptosis.

8. A pharmaceutical composition, comprising
an organoselenium benzimidazole compound of formula (I) or a pharmaceutically acceptable salt thereof; and
a pharmaceutically acceptable carrier and/or excipient,

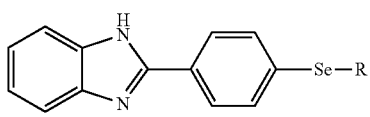
(I)

wherein
R is at least one selected from the group consisting of an alkyl group having 1 to 6 carbon atoms, an unsubstituted benzyl group, a para halo-substituted benzyl group, and an allyl group.

9. The pharmaceutical composition of claim 8, wherein the alkyl group having 1 to 6 carbon atoms is at least one selected from the group consisting of methyl, ethyl, and n-propyl.

10. The pharmaceutical composition of claim 8, wherein the organoselenium benzimidazole compound of formula (I) is at least one selected from formulae (II) to (VII)

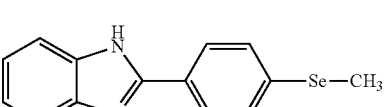
(II)

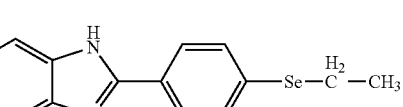
(III)

-continued

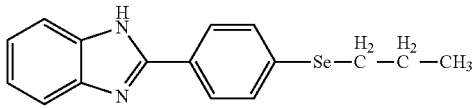
(IV)

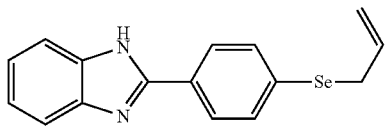
(V)

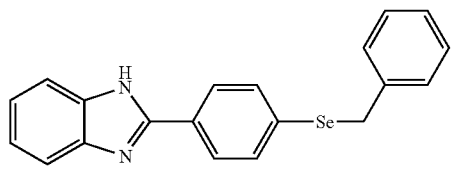
(VI)

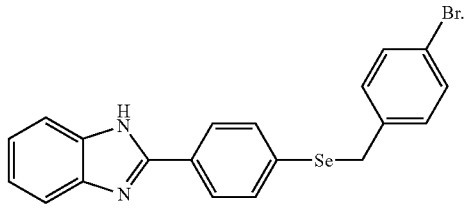
(VII)

11. The pharmaceutical composition of claim 8, wherein the pharmaceutically acceptable carrier and/or excipient is at least one selected from the group consisting of a buffer, an inorganic salt, a synthetic fatty acid, a vegetable oil, a fatty ester, a surfactant, and a polymer.

12. The pharmaceutical composition of claim 11, further comprising one or more of a sweetener, a flavoring, and a colorant.

13. The pharmaceutical composition of claim 8, wherein the pharmaceutical composition is formulated for at least one mode of administration selected from the group consisting of oral administration, parenteral administration, rectal administration, topical administration, transdermal administration, intralesional administration, and inhalation administration.

14. A method of forming an organoselenium benzimidazole compound of formula (1),

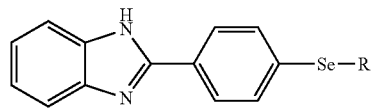
(I)

where R is at least one selected from the group consisting of an alkyl group having 1 to 6 carbon atoms, an unsubstituted benzyl group, a para halo-substituted benzyl group, and an allyl group,
the method comprising
reacting o-phenylenediamine and 4,4'-diselanediyldibenzoic acid with an acid to form 1,2-bis(4-(1H-benzo[d]imidazol-2-yl)phenyl)diselane; and
reacting the 1,2-bis(4-(1H-benzo[d]imidazol-2-yl)phenyl)diselane with at least one selected from the group consisting of an alkyl halide having 1 to 6 carbon atoms, an unsubstituted benzyl halide, a para halo-substituted benzyl halide, and an allyl halide, a hydride reducing agent, and a base to form the organoselenium benzimidazole compound of formula (1).

15. The method of claim 14, wherein the acid comprises acetic acid, polyphosphoric acid, and water.

16. The method of claim 14, wherein the reacting o-phenylenediamine and 4,4'-diselanediyldibenzoic acid with an acid is performed at 160 to 200° C.

17. The method of claim 14, wherein the alkyl group having 1 to 6 carbon atoms is at least one selected from the group consisting of methyl, ethyl, and n-propyl.

18. The method of claim 14, wherein the hydride reducing agent is sodium borohydride.

19. The method of claim 14, wherein the base is an alkali metal hydroxide base.

* * * * *